United States Patent
Terasaka et al.

(10) Patent No.: US 7,259,274 B2
(45) Date of Patent: Aug. 21, 2007

(54) METHOD OF PRODUCING ALIPHATIC NITRILE

(75) Inventors: Michio Terasaka, Wakayama (JP); Tetsuaki Fukushima, Wakayama (JP)

(73) Assignee: Kao Corporation, Tokyo (JP)

( * ) Notice: Subject to any disclaimer, the term of this patent is extended or adjusted under 35 U.S.C. 154(b) by 385 days.

(21) Appl. No.: 10/936,745

(22) Filed: Sep. 9, 2004

(65) Prior Publication Data

US 2005/0059836 A1     Mar. 17, 2005

(30) Foreign Application Priority Data

Sep. 17, 2003    (JP)  ............... 2003-324101

(51) Int. Cl.
*C07C 253/00*    (2006.01)
*C07C 63/30*    (2006.01)

(52) U.S. Cl. ...................... 558/311; 564/490

(58) Field of Classification Search ............... 558/311; 564/490
See application file for complete search history.

(56) References Cited

U.S. PATENT DOCUMENTS

| 2,993,926 A | 7/1961 | Stenberg et al. |
| 6,005,134 A | 12/1999 | Terasaka et al. |
| 6,080,891 A | 6/2000 | Terasaka et al. |

FOREIGN PATENT DOCUMENTS

| EP | 0 668 100 A1 | 8/1995 |
| JP | 58-39653 | 3/1983 |
| JP | 4-208260 | 7/1992 |
| JP | 10-195035 | 7/1998 |
| JP | 2000-80069 | 3/2000 |
| WO | WO 03/070688 A1 | 8/2003 |

*Primary Examiner*—Kamal A. Saeed
(74) *Attorney, Agent, or Firm*—Oblon, Spivak, McClelland, Maier & Neustadt, P.C.

(57) ABSTRACT

An aliphatic nitrile is prepared by a process of reacting an aliphatic carboxylic acid, an aliphatic dicarboxylic acid or an alkyl ester thereof, wherein the alkyl group has 1 to 5 carbon atoms, with ammonia in the presence of a catalyst of titanium oxide supported on solid silica.

13 Claims, No Drawings

METHOD OF PRODUCING ALIPHATIC NITRILE

FIELD OF THE INVENTION

The present invention relates to a catalyst which reacts an aliphatic carboxylic acid, an aliphatic dicarboxylic acid or an alkyl ester (the number of carbons of the alkyl group: 1 to 5) of these acids with ammonia to produce an aliphatic nitrile, to a method of producing an aliphatic nitrile by using this catalyst and a method of producing an aliphatic amine from the aliphatic nitrile produced by this method.

BACKGROUND OF THE INVENTION

Generally, a method in which an aliphatic carboxylic acid or its derivative is reacted with ammonia is known industrially as a method of producing an aliphatic nitrile. This method is roughly classified by reaction form into a gas phase method and a liquid phase method. JP-A 4-208260 discloses, as the vapor phase method, a method in which an aliphatic carboxylic acid or its derivative which has been vaporized in advance is reacted catalytically with ammonia at a temperature of 250 to 600° C. by using, as a catalyst, an oxide of Zr, Ta, Ga, In, Sc, Nb, Hf, Fe, Zn or Sn. JP-A10-195035 discloses a method in which an aliphatic carboxylic acid or its alkyl ester which has been vaporized in advance is reacted catalytically with ammonia at a temperature of 200 to 400° C. by using zirconium oxide poisoned by a metal polyvalent cation.

In the case of reacting in the liquid phase method, on the other hand, an aliphatic carboxylic acid or its derivative is dissolved under heating in the presence of a catalyst and ammonia gas is blown into the solution to react both in a batch system or in a continuous system. For example, JP-A 58-39653 discloses a method in which iron or an iron compound is used to react at 150 to 290° C.

JP-A 2000-80069 discloses a production method using a complex oxide which is sparingly soluble in a reaction solution and obtained by compounding an oxide of one or more elements selected from the group consisting of silicone, niobium, zirconium, tantalum, gallium and gelmanium with titanium oxide at a reaction temperature of 300° C. or less.

U.S. Pat. No. 6,080,891 and U.S. Pat. No. 6,005,134 disclose methods in which an aliphatic carboxylic acid, aliphatic carboxylic acid lower alkyl ester or aliphatic glyceride is reacted with ammonia by using an oxide catalyst obtained by using titanium oxide as its major component and by compounding an oxide of one or more elements selected from the group consisting of niobium, zirconium, tantalum, gallium and germanium, and also, a method of producing an amine by hydrogenating the aliphatic nitrile. A metal alkoxide is used as a titanium source.

SUMMARY OF THE INVENTION

The present invention provides a method of producing an aliphatic nitrile, including reacting an aliphatic carboxylic acid, an aliphatic dicarboxylic acid or an alkyl ester thereof, wherein the alkyl group of the alkyl ester has 1 to 5 carbon atoms, with ammonia in the presence of a catalyst of titanium oxide supported on solid silica.

The present invention provides a method of producing an aliphatic amine, including reacting an aliphatic carboxylic acid, an aliphatic dicarboxylic acid or an alkyl ester thereof, wherein the alkyl group of the alkyl ester has 1 to 5 carbon atoms, with ammonia in the presence of a catalyst of titanium oxide supported on solid silica to obtain an aliphatic nitrile and then hydrogenating the aliphatic nitrile with a hydrogenating catalyst.

The present invention provides a catalyst for producing an aliphatic nitrile, obtained by treating silica gel or silica sol with titanium oxysulfate.

DETAILED DESCRIPTION OF THE INVENTION

In the reactions described in JP-A 4-208260 and JP-A10-195035, it is necessary to gasify the fatty acid or fatty acid derivative which are raw materials and these methods have the drawbacks that they are inferior to a liquid phase method in which a large energy cost is required.

In the reaction of JP-A 58-39653, the catalyst is diluted in the aliphatic carboxylic acid and this eluted product acts as a reaction inhibitive factor in, for example, this method of producing an aliphatic amine from an aliphatic nitrile by a hydrogenating reaction. For this, new equipment is required to separate and recover this eluted product, and also, the yield of the aliphatic nitrile is reduced. Therefore, this method is undesirable as a method of producing an aliphatic nitrile.

The catalyst described in JP-A 2000-80069 has yet room for improvement industrially because alkoxides of these metals which are the raw materials used to prepare the catalyst are expensive and have only insufficient reactivity though the elution of the catalyst in an aliphatic carboxylic acid is certainly restricted.

The present invention provides a catalyst for producing an aliphatic nitrile, the catalyst having enough reactivity and being industrially advantageous in the point that it can be produced economically in the situation that an aliphatic carboxylic acid, an aliphatic dicarboxylic acid or an alkyl ester (the alkyl group with 1 to 5 carbon atoms) of these carboxylic acids is reacted with ammonia in a liquid phase system, a method of producing an aliphatic nitrile by using the catalyst and a method of producing an aliphatic amine by hydrogenating the aliphatic nitrile, produced by the above method, by using a hydrogenating catalyst.

The present invention relates to a method of producing an aliphatic nitrile in a liquid phase system from an aliphatic carboxylic acid, an aliphatic dicarboxylic acid or an alkyl ester (the alkyl group with 1 to 5 carbon atoms) of these carboxylic acids and ammonia by using a catalyst which can be economically produced, has superior reactivity and is prepared by supporting titanium oxide on solid silica. The present invention also relates to a method of producing an aliphatic amine, the method including preparing an aliphatic nitrile in a liquid phase from an aliphatic carboxylic acid, an aliphatic dicarboxylic acid or an alkyl ester (the alkyl group with 1 to 5 carbon atoms) of these carboxylic acids and ammonia in the above production method and in succession, running a hydrogenating reaction using a hydrogenating catalyst.

The preferred catalyst according to the present invention is industrially advantageous in the point that it can be produced at low costs as a catalyst used to react an aliphatic carboxylic acid or its lower alkyl ester with ammonia in a liquid phase system. Also, an aliphatic nitrile can be produced at a low cost by using a catalyst having sufficient reactivity. Moreover, the resulting aliphatic nitrile is hydrogenated using a hydrogenating catalyst, whereby an aliphatic amine can be produced at a high yield.

The present invention relates to a production method using a titanium oxide catalyst supported on solid silica. The present invention may use inexpensive raw materials such as titanium sulfate and silica sol. The acidic quantity of the catalyst is high. The productivity can be improved.

The method of producing an aliphatic nitrile according to the present invention relates to a method in which an aliphatic carboxylic acid, an aliphatic dicarboxylic acid or an alkyl ester (the number of carbons of the alkyl group: 1 to 5) of these acids is reacted with ammonia by using a catalyst prepared by supporting titanium oxide on solid silica. Examples of a method of supporting titanium oxide on a solid silica include methods in which insoluble silica is added to a solution of a compound which is to be a raw material of titanium oxide and the solution is heated to the temperature at which the thermal hydrolysis of the compound which is to be a raw material of titanium oxide is caused or an additive such as ammonia is added to cause neutralization hydrolysis to thereby precipitate titanium oxide. The compound which is to be the raw material of titanium oxide is preferably a sulfate, nitrate, halide of alkoxide of titanium, more preferably a sulfate of titanium and even more preferably titanium oxysulfate with the intention of improving the acidic quantity of the catalyst. Examples of the silica include silica sol and silica gel. Among these compounds, those having an average particle diameter of 5 to 30 μm are preferable and those having an average particle diameter of 10 to 30 μm are more preferable because titanium oxide is precipitated on the silica so that the specific surface area is increased. Although the solvent may be ion exchange water or distilled water, an aqueous solution of sulfuric acid or ammonium sulfate is preferable for the purpose of improving the acidic quantity of the catalyst.

The acidic quantity of the catalyst of the present invention is preferably 0.6 to 4.0 mmol/g, more preferably 1.0 to 3.5 mmol/g and even more preferably 1.5 to 3.0 mmol/g. The acidic quantity can be controlled under the presence of a controlled amount of a sulfuric acid ion or the like in the solution when preparing the catalyst. The amount of the sulfuric acid ion existing in the catalyst is as follows in terms of weight ratio of sulfur to titanium from the viewpoint of catalyst activity: sulfur/titanium=preferably 0.001/1 to 0.06/1, more preferably 0.001/1 to 0.02/1 and even more preferably 0.002/1 to 0.015/1. Sulfur is quantitatively determined by adding a combustion improver (tungsten (0.7 g)+tin (0.3 g)) to 0.1 g of a sample to measure by a combustion-infrared ray-absorbing method using CS-444 manufactured by Leco.

The acidic quantity of the catalyst is preferably measured by a temperature rise-ammonia desorption device manufactured by Nippon Bell. The measuring method is as follows. First, about 0.1 g of a sample of which the acidic quantity is known is treated at 110° C. for one hour under a helium stream (50 ml/min) and then cooled to 50° C. to make ammonia adhere (2.67 kPa, 10 min) to the sample, followed by vacuum aspiration for 4 hours. After the treatment under vacuum, the sample is heated to 600° C. at a rate of 5 ml/min under a helium stream (50 ml/min). Using a straight line connecting the straight point to the final point of the desorption peak of ammonia as a base line, a correction factor is calculated from the ammonia desorption peak area obtained at this time and the acidic quantity of the catalyst per 1 g of the sample. Next, the catalyst of the present invention is measured in the same method. Then, the resulting ammonia desorption peak area is multiplied by the correction factor and divided by the amount of the sample to calculate the acidic quantity of the catalyst.

The specific surface area of the catalyst used in the present invention is preferably 100 to 500 $m^2$/g, more preferably 200 to 500 $m^2$/g and even more preferably 250 to 500 $m^2$/g from the viewpoint of reactivity. The specific surface area of the catalyst is measured using Flowsoap 2300 model (manufactured by Shimadzu Corporation) to calculate from nitrogen gas adsorption at low temperatures by using a BET equation. The measuring method is as follows.

The sample is charged in a measuring cell such that the total surface area to be sampled is about 0.5 to 25 $m^2$ and degassed at 100° C. for 10 minutes. Then, the cell is cooled by liquid nitrogen to allow nitrogen to adsorb.

After the adsorption is completed, the cell is immersed in water at ambient temperature to return the temperature of the sample to ambient temperature. The surface area of the sample measured based on the amount of nitrogen desorbed from the sample at this time is obtained. The measured value is divided by the weight of the sample to find the specific surface area of the catalyst.

As to each proportion of the structural elements of the catalyst used in the present invention, the proportion of silica is preferably 1 to 15 weight %, more preferably 2 to 10 weight % and even more preferably 2 to 8 weight % as silicon in view of reactivity. The ratio (Si/Ti) by weight of silicon to titanium is preferably 2/100 to 35/100, more preferably 3/100 to 30/100 and even more preferably 4/100 to 25/100. A preferred method of quantitatively measuring titanium and silica among the structural elements of the catalyst is as follows. 5 g of lithium tetraborate and a releasing agent ($LiCO_3$:LiBr:$LiNO_3$=5:1:5) are added to 0.1 g of the catalyst and the mixture is alkali-fused at 1050° C. to make glass beads. A wavelength dispersion type fluorescent X-ray analyzer (ZSX100e, manufactured by Rigaku Corporation) is used to measure each element quantitatively in the following conditions: in the case of titanium, voltage: 50 kV, current: 50 mA, LiF spectral crystal, SC (scintillation counter) detector, detecting angle: 86.110 deg, and in the case of silicon, voltage: 50 kV, current: 50 mA, PET spectral crystal, PC (gas flow proportional counter) detector, detecting angle: 108.995 deg. The resulting X-ray intensity is collated with a calibration curve obtained from a material prepared by blending titanium oxide (99.9%) with silica (99.9%) according to an intended concentration to determine each quantitative value of titanium and silicon.

The catalyst prepared in this manner may be either calcined or not calcined. It is however undesirable to calcine the catalyst from the viewpoint of specific surface area and catalyst activity. When the catalyst is calcined, it is calcined preferably at 400° C. or less, more preferably 300° C. or less and even more preferably 200° C. or less.

The catalyst with titanium oxide supported on solid silica which is used to produce the aliphatic nitrile of the present invention may contain components, such as oxides of niobium, zirconium, tantalum, gallium and germanium, which do not inhibit the reaction in the invention.

Examples of the aliphatic carboxylic acid, aliphatic dicarboxylic acid or alkyl ester (the alkyl group with 1 to 5 carbon atoms) of these acids include straight-chain or branched saturated or unsaturated aliphatic monocarboxylic or dicarboxylic acids having 6 to 22 carbon atoms and alkyl esters (the alkyl group with 1 to 5 carbon atoms) of these acids. Here, specific examples of the alkyl group having 1 to 5 carbon atoms include methyl, ethyl, propyl and isopropyl and particularly, methyl is preferable.

These aliphatic carboxylic acids, aliphatic dicarboxylic acids or alkyl esters (the alkyl group has 1 to 5 carbon atoms)

of these acids may be used either independently or in combinations of two or more.

Specific examples of the aliphatic carboxylic acids and aliphatic dicarboxylic acids include caproic acid, caprylic acid, capric acid, lauric acid, myristic acid, palmitic acid, stearic acid, arachic acid, behenic acid, dimethyloctanic acid, butylheptylnonanoic acid, hexenoic acid, octenoic acid, decenoic acid, dodecenoic acid, tetradecenoic acid, hexadecenoic acid, octadecenoic acid, eicosenoic acid, docosenoic acid, adipic acid, azelaic acid, sebacic acid, decamethylenedicarboxylic acid, hexadecamethylenedicarboxylic acid and octadecamethylenedicarboxylic acid.

Specific examples of the alkyl esters (the alkyl group with 1 to 5 carbon atoms) of aliphatic carboxylic acids include methyl, ethyl, propyl or isopropyl esters of the aforementioned aliphatic carboxylic acids or aliphatic dicarboxylic acids.

The reaction in the method of producing the aliphatic nitrile according to the present invention may be run in a batch system, semi-batch system or continuous system using a suspension bed, and also in a fixed-bed flow system. In the production method using a batch or semi-batch system, the aliphatic nitrile may be produced using a method in which the aliphatic acid is dissolved, a fixed amount of the catalyst is charged, the atmosphere of a reaction vessel is thoroughly replaced by nitrogen, then the system is raised up to the reaction temperature and then ammonia gas is flowed into the reaction vessel. In the production method using a continuous system or fixed-bed continuous system, the aliphatic nitrile may be produced using a method in which the catalyst is filled and the system is raised up to the reaction temperature and then a dissolved aliphatic carboxylic acid, aliphatic dicarboxylic acid or alkyl ester of these acids and ammonia gas are flowed into the system.

As to the pressure during reaction, the reaction is run usually under slightly pressurized condition. However, the reaction may be run under normal pressure. The production temperature of the aliphatic nitrile of the present invention is preferably 180 to 350° C., more preferably 230 to 320° C. and even more preferably 250 to 300° C. Also, the reaction time is preferably 3 to 15 hours, more preferably 4 to 12 hours and even more preferably 6 to 10 hours. The amount of ammonia to be used in the present invention is preferably 1 to 100 mol, more preferably 2 to 50 mol and even more preferably 2 to 20 mol based on one mol of the aliphatic carboxylic acid, aliphatic dicarboxylic acid or alkyl ester of these acids. Although the catalyst may be charged in a desired amount, the amount of the catalyst is in a range from 0.05 to 20 weight %, preferably 0.1 to 15 weight % and more preferably 0.1 to 10 weight % based on the aliphatic carboxylic acid, aliphatic dicarboxylic acid or alkyl ester of these acids.

Moreover, the preferred method of producing an aliphatic amine according to the present invention is a method in which the aliphatic nitrile produced in the above method is hydrogenated using a hydrogenating catalyst without performing a refining process such as distillation. The catalyst of the present invention is not almost dissolved in the raw material aliphatic carboxylic acid, with the result that the aliphatic nitrile produced in the method of the present invention ensures that a hydrogenating reaction is initiated efficiently even if the aliphatic amine is not refined by for example, distillation, whereby an aliphatic amine can be produced.

As the catalyst used in the method of producing an aliphatic amine of the present invention, a known hydrogenating catalyst, for example, a cobalt type catalyst, nickel type catalyst, copper type catalyst or precious metal type catalyst may be used. A catalyst containing nickel, cobalt and/or ruthenium as its major component is preferably used and a Raney type catalyst is more preferably used. Also, the catalyst may further contain other metals such as aluminum, zinc and silicon. The catalyst may also contain a metal selected from chromium, iron, cobalt, manganese, tungsten and molybdenum. On the other hand, a complete solid catalyst or a supporting type solid catalyst, for example, those in which nickel, cobalt, ruthenium or the like is supported on $Al_2O_3$, $TiO_2$, $ZrO_2$ or $MgO/Al_2O_3$ may also be used. The amount of the hydrogenating catalyst to be used is preferably 0.05 to 5 weight parts and preferably 0.1 to 3 weight parts based on 100 parts by weight of aliphatic nitrile.

The pressure, specifically, hydrogen pressure when the aliphatic amine of the present invention is produced is preferably 0.3 to 5 Mpa, more preferably 1.0 to 4 MPa and even more preferably 1.5 to 3 Mpa. The reaction temperature is preferably 50 to 200° C., more preferably 80 to 170° C. and even more preferably 100 to 140° C. and it is preferable to raise the reaction temperature continuously or step by step when a hydrogenating reaction is run. Also, the reaction time is preferably 1 to 15 hours, more preferably 2 to 12 hours and even more preferably 3 to 10 hours.

The following examples further describe and demonstrate embodiments of the present invention. The examples are given solely for the purpose of illustration and are not to be construed as limitations of the present invention.

EXAMPLES

The present invention will be explained in detail by way of examples.

Preparation Example 1 of a Catalyst

A 1 L flask was charged with 34.0 g of titanium oxysulfate and 270 g of an aqueous silica sol solution (3 g as silica) and the mixture was heated to 90° C. while stirring.

After it was confirmed that titanium oxysulfate was dissolved, aqueous ammonia was added dropwise to the solution (90° C.) to neutralize the solution, which was then stirred for 2 hours. The resulting precipitated product was filtered and washed with 1 liter of ion exchange water four times, followed by drying at 110° C. overnight. A composition analysis using fluorescent X-ray analysis, measurement of ammonia temperature programmed-desorption and measurement of specific surface area using a BET method were made. Thus, a catalyst A having the composition, acidic quantity and specific surface area shown in Table 1 was obtained.

Preparation Example 2 of a Catalyst

Catalysts B and C shown in Table 1 were obtained by repeating the same procedures as in Preparation Example 1 except that the amount of the silica sol and the number of water-washing and filtering operations were altered to alter the content of S.

Preparation Example 3 of a Catalyst

The catalyst obtained in Preparation Example 1 was calcined at 200° C. or 300° C. for 3 hours to obtain catalysts D and E shown in Table 1.

(Comparative Catalyst)

The same procedures as in Preparation Example 1 were repeated except that no silica sol was added, to obtain a catalyst F. The composition, acidic quantity and specific surface area of the catalyst F are shown in Table 1. In order to obtain a catalyst in which titanium oxide was not supported on solid silica though the catalyst contained silicon and titanium, a preparative operation was supported out in the procedures disclosed in Example 1 described in the publication of JP-A No. 2000-80069 to obtain a catalyst G having the composition, acidic quantity and specific surface area shown in Table 1.

TABLE 1

|  |  | Catalyst of the present invention | | | | | Comparative catalyst | |
|---|---|---|---|---|---|---|---|---|
|  |  | A | B | C | D | E | F | G |
| Catalyst | Ti | 49 | 55 | 43 | 49 | 49 | 59 | 56 |
| composition | S | 0.35 | 0.30 | 0.23 | 0.27 | 0.14 | 0.08 | 0 |
| (%) | Si | 7.2 | 2.2 | 11.8 | 7.2 | 7.2 | 0 | 2.1 |
| Acidic quantity of the catalyst (mmol/g) |  | 2.0 | 1.9 | 1.7 | 1.9 | 1.0 | 0.5 | 0.9 |
| Specific surface area (m$^2$/g) |  | 296 | 328 | 289 | 269 | 180 | 265 | 250 |
| Ratio by weight of Si/Ti ×10$^{-2}$ |  | 14.7 | 4.0 | 27.4 | 14.7 | 14.7 | — | 3.8 |

Example 1

1.0 g of the catalyst A and 500 g of stearic acid were mixed with each other in a four-neck flask equipped with a stirrer, a gas introduction pipe, a temperature gage and a dehydrator. The reaction mixture was reacted at a reaction temperature 300° C. while introducing 1000 ml/min of ammonia gas. The resulting reaction product was subjected to compositional analysis using gas chromatography (gas chromatograph: HEWLETT PACKARD Series 5890, column: DB-5 (inside diameter×length: 0.53 mm×15 m), manufactured by J & W) to measure the amount of stearonitrile to be produced. The results are shown in Table 2.

Examples 2 to 5, Comparative Examples 1 and 2

The catalysts B, C, D and E of the present invention or the comparative catalysts F, G and H were respectively used in place of the catalyst A in Example 1 to run reaction in the same manner as in Example 1 except for the reaction conditions shown in Table 2 and each reaction product was analyzed in the same manner as in Example 1. The results are shown in Table 2. It is to be noted that the reaction termination time is the time required from when ammonia gas is introduced until the amount of the aliphatic amide to be produced measured by gas chromatography becomes 0.

TABLE 2

|  | Catalyst | Reaction temperature (° C.) | Amount of the nitrile produced after three hours (%) | Reaction termination time (h) |
|---|---|---|---|---|
| Example 1 | A | 300 | 99.5 | 3.5 |
| Example 2 | B | 300 | 99.1 | 3.8 |
| Example 3 | C | 300 | 97.2 | 4.3 |
| Example 4 | D | 300 | 98.1 | 3.9 |
| Example 5 | E | 300 | 93.6 | 4.7 |

TABLE 2-continued

|  | Catalyst | Reaction temperature (° C.) | Amount of the nitrile produced after three hours (%) | Reaction termination time (h) |
|---|---|---|---|---|
| Comparative example 1 | F | 300 | 86.2 | 5.3 |
| Comparative example 2 | G | 300 | 92.6 | 4.8 |

Example 6

The same procedures as in Example 1 were conducted except that lauric acid was used instead of stearic acid and 1350 ml/min of ammonia gas was introduced over 8 hours to react at 260° C. in Example 1. The yield of laurylonitrile measured by gas chromatography was 94.5%.

Example 7

The same procedures as in Example 1 were conducted except that methyl stearate was used instead of stearic acid in Example 1. The yield of stearonitrile measured by gas chromatography after 8 hours reaction was 98.7%.

Comparative Example 3

The same procedures as in Example 7 were conducted except that the catalyst G was used in place of the catalyst A in Example 7. The yield of stearonitrile measured by gas chromatography after 8 hours reaction was 86.6%.

Example 8

An autoclave was charged with 450 g of the product obtained in Example 1, 1.6 g of a Raney nickel catalyst as a hydrogenating catalyst, 0.9 g of 48% NaOH and 7.8 g of ion exchange water and the atmosphere in the vacant part of the autoclave was substituted with hydrogen to adjust the hydrogen pressure of the system to 1.9 MPa. Then, the mixture was raised at 135° C. and reacted for 3 hours. The resulting reaction product was subjected to compositional analysis using gas chromatography (gas chromatograph: HEWLETT PACKARD, column: Ultra-2 (inside diameter× length: 0.53 mm×15 m), manufactured by HEWLETT PACKARD) to measure the amount of stearylamine to be produced, to find that the yield was 98.2%.

Example 9

The same procedures as in Example 1 were conducted except that oleic acid (Lunac O-A, manufactured by Kao Corporation) was used instead of stearic acid in Example 1. The yield of nitrile measured by gas chromatography after 4 hours reaction was 98.4%.

The invention claimed is:

1. A method of producing an aliphatic nitrile, comprising the step of:
reacting an aliphatic carboxylic acid, an aliphatic dicarboxylic acid or an alkyl ester thereof, wherein the alkyl group has 1 to 5 carbon atoms, with ammonia in the presence of a catalyst of titanium oxide supported on solid silica.

2. The method according to claim 1, wherein the quantity of acid in the catalyst ranges from 0.6 to 4.0 mmol/g.

3. The method according to claim 2, wherein the quantity of acid in the catalyst ranges from 1.0 to 3.5 mmol/g.

4. The method according to claim 1, wherein the acid that is present in the catalyst is sulfuric acid which is present in terms of a weight ratio of sulfur of the acid to titanium ranging from 0.001/1 to 0.06/1.

5. The method according to claim 1, wherein the specific surface area of the catalyst ranges from 100 to 500 $m^2/g$.

6. The method according to claim 5, wherein the specific surface area of the catalyst ranges from 200 to 500 $m^2/g$.

7. The method according to claim 1, wherein the ratio of Si/Ti of the catalyst ranges from 2/100 to 35/100.

8. The method according to claim 1, wherein the catalyst further comprises on oxide of niobium, zirconium, tantalum, gallium or germanium.

9. The method according to claim 1, wherein the aliphatic carboxylic acid or aliphatic dicarboxylic acid is selected from the group consisting of caproic acid, caprylic acid, capric acid, lauric acid, myristic acid, palmitic acid, stearic acid, arachic acid, behenic acid, dimethyloctanic acid, butyi-heptylnonanoic acid, hexenoic acid, octenoic acid, decenoic acid, dodecenoic acid, tetradecenoic acid, hexadecenoic acid, octadecenoic acid, eicosenoic acid, docosenoic acid, adipic acid, azelaic acid, sebacic acid, decamethylenedicarboxylic acid, hexadecamethylenedicarboxylic acid and octadecamethylenedicarboxylic acid.

10. The method according to claim 1, wherein the amount of ammonia ranges from 1 to 100 mol.

11. The method according to claim 1, wherein the catalyst is obtainable by treating silica gel or silica sol with titanium oxysulfate.

12. A method of producing an aliphatic amine, comprising the steps of:
reacting an aliphatic carboxylic acid, an aliphatic dicarboxylic acid or an alkyl ester thereof, wherein the alkyl group has 1 to 5 carbon atoms, with ammonia in the presence of a catalyst of titanium oxide supported on solid silica to obtain an aliphatic nitrile; and then
hydrogenating the aliphatic nitrile with a hydrogenating catalyst.

13. The method according to claim 12, wherein the hydrogenation reaction of the nitrile compound is conducted over a catalyst based on cobalt, nickel, copper or a noble metal under a hydrogen pressure ranging from 0.3 to 5 Mpa at a temperature ranging from 50 to 2000° C.

* * * * *